(12) United States Patent
Messerges

(10) Patent No.: US 8,128,570 B2
(45) Date of Patent: Mar. 6, 2012

(54) PERSONALIZED FLUID ASSESSMENT

(75) Inventor: Joanne L. Messerges, Wauwatosa, WI (US)

(73) Assignee: The General Electric Company, Schenectady, NY (US)

( * ) Notice: Subject to any disclaimer, the term of this patent is extended or adjusted under 35 U.S.C. 154(b) by 972 days.

(21) Appl. No.: 12/117,485

(22) Filed: May 8, 2008

(65) Prior Publication Data

US 2009/0281434 A1    Nov. 12, 2009

(51) Int. Cl.
*A61B 5/02* (2006.01)

(52) U.S. Cl. ...................................................... 600/485

(58) Field of Classification Search ......................... None
See application file for complete search history.

(56) References Cited

U.S. PATENT DOCUMENTS

| 6,974,418 | B1 | 12/2005 | Hutchinson et al. |
| 2002/0151805 | A1 | 10/2002 | Sugo et al. |
| 2005/0222514 | A1 | 10/2005 | Sugo et al. |
| 2008/0045845 | A1 | 2/2008 | Pfeiffer et al. |
| 2009/0198140 | A1 | 8/2009 | Riobo Aboy et al. |

FOREIGN PATENT DOCUMENTS

EP    1 155 658 A2    11/2001

OTHER PUBLICATIONS

GB Search Report dated Sep. 7, 2009.

*Primary Examiner* — Tracy Vivlemore
(74) *Attorney, Agent, or Firm* — Andrus, Sceales, Starke & Sawall, LLP

(57) ABSTRACT

A system and method of monitoring the fluid status of a patient. The system may include a patient monitor that receives blood pressure data. A first fluid model receives the blood pressure data, and a personalized fluid model is derived from the application of the blood pressure data to the first fluid model. An estimation of the patient's fluid status may be derived from the personalized fluid model. The method may include the steps of measuring a first blood pressure value, creating a personalized fluid model, measuring a second blood pressure value, applying the second blood pressure value to the personalized fluid model; and deriving an estimation of the fluid status of the patient.

11 Claims, 3 Drawing Sheets

PERSONALIZED FLUID ASSESSMENT

FIELD OF THE DISCLOSURE

The present disclosure relates to the field of monitoring patient physiological parameters. More specifically, the present disclosure relates to the indirect monitoring of patient fluid status.

BACKGROUND

In critical care and other medical care situations, the parameter of fluid status is an important parameter to be monitored. The patient's fluid status generally refers to the volume, or change in volume, of blood presently in the circulatory system of the patient.

A change in the patient's blood volume due to hypervolemia or excessive fluid, or hypovolemia, or reduced fluid volume, can result in various autonomic responses by the organ systems of the patient. As baroreceptors detect a change in the fluid volume, the organ function similarly changes to accommodate for the addition or loss of fluid. These autonomic responses attempt to maintain appropriate bodily function in response to the change in fluid volume.

Another effect of a change in fluid volume is the impact on pharmacokinetic and pharmacodynamic models used by clinicians in determining the proper drug dosage, the resulting drug concentration in the body, and the body's metabolism of the drugs currently in its system.

One exemplary situation where the fluid status of the patient is an important physiological parameter is that of a critical care situation, such as during an invasive surgery. During such surgery, the anesthesiologist must continuously monitor the patient's vital signs to determine the proper drug concentrations to be delivered to the patient. The vital signs, including the patient's heart rate, temperature, blood pressure and breath rate, all may be affected by the patient's autonomic response to a change in fluid status. These vital signs are all important to determine the proper drug concentrations and fluids to be delivered to the patient. This is conducted in a situation in which the patient may experience significant changes in fluid status. Sources of fluid status change include bleeding, dehydration via tissue exposed to air at the surgical site, urine production, and the administration of intravenous fluids, including crystalloids or colloids.

Current techniques for monitoring the patient's fluid status are limited for being complex, inaccurate, or subjective. Techniques such as measuring capillary refill time (or the time that it takes for blood to return to nail bed tissue after pressure has been applied) are subjective and qualitative evaluations of fluid status. Techniques such as transesophagal echo that utilize ultrasound to monitor fluid movement in the thoracic cavity are invasive, especially in situations when the patient requires mechanical ventilation. Alternatively, an estimation of fluid status may be made by actively charting all of the fluid into and out of the patient. This estimation is labor intensive and is limited in its ability to provide timely fluid status levels.

BRIEF DISCLOSURE

The present disclosure relates to the field of patient fluid status monitoring. Embodiments of a system for estimating the fluid status of a patient are described in more detail herein. In an embodiment, a patient monitor receives patient physiological data. This patient physiological data is transferred into a first fluid model in order to calibrate the first fluid model to create a personalized fluid model based on the monitored physiological data. The personalized fluid model may then be used to derive an estimation of the patient's fluid status at a later time or date.

Embodiments of a method of estimating the fluid status of a patient are also disclosed herein. Such embodiments may include the step of obtaining a fluid model. Next, a first blood pressure value is measured. The fluid model and, the first blood pressure value, are used to create a personalized fluid model for the patient. Next, a second blood pressure value is measured and applied to the personalized fluid model. Finally, a patient fluid status estimated value is calculated from the personalized fluid model.

DETAILED DISCLOSURE

Systolic pressure variation (SPV) is a physiological phenomenon found in the continuous arterial blood pressure of a patient receiving positive pressure ventilation (PPV). The PPV causes a cyclical change in intra-thoracic pressure experienced by the patient. The increase in intra-thoracic pressure during inhalation causes a decrease in the left ventricular after load by increasing the pressure gradient between the aorta and the systemic vasculature. These effects attenuate as the intra-thoracic pressure decreases during exhalation. The additional pressure also decreases the venus return by decreasing the pressure gradient between the vena cava and the right atrium. The overall effect seen in the monitored arterial blood pressure is that an increase in the systolic, or maximum, blood pressure ($\Delta$ up) is found during the periods of inhalation, while a decrease in the measured systolic pressure ($\Delta$ down) is found during exhalation.

The difference between the measured systolic pressure during inhalation versus exhalation is the measured systolic pressure variation (SPV). Clinical tests have shown a correlation between the change in measured SPV and a change in the fluid status of the patient. Typically, a reduction in the fluid volume status of the patient results in an increase in the measured SPV. While SPV is used in the present disclosure, it is to be understood that other dynamic pressure variables may be used in alternative embodiments. One non-limiting example of another dynamic pressure variable that may be used is that of pulse pressure variation.

Figure 1:
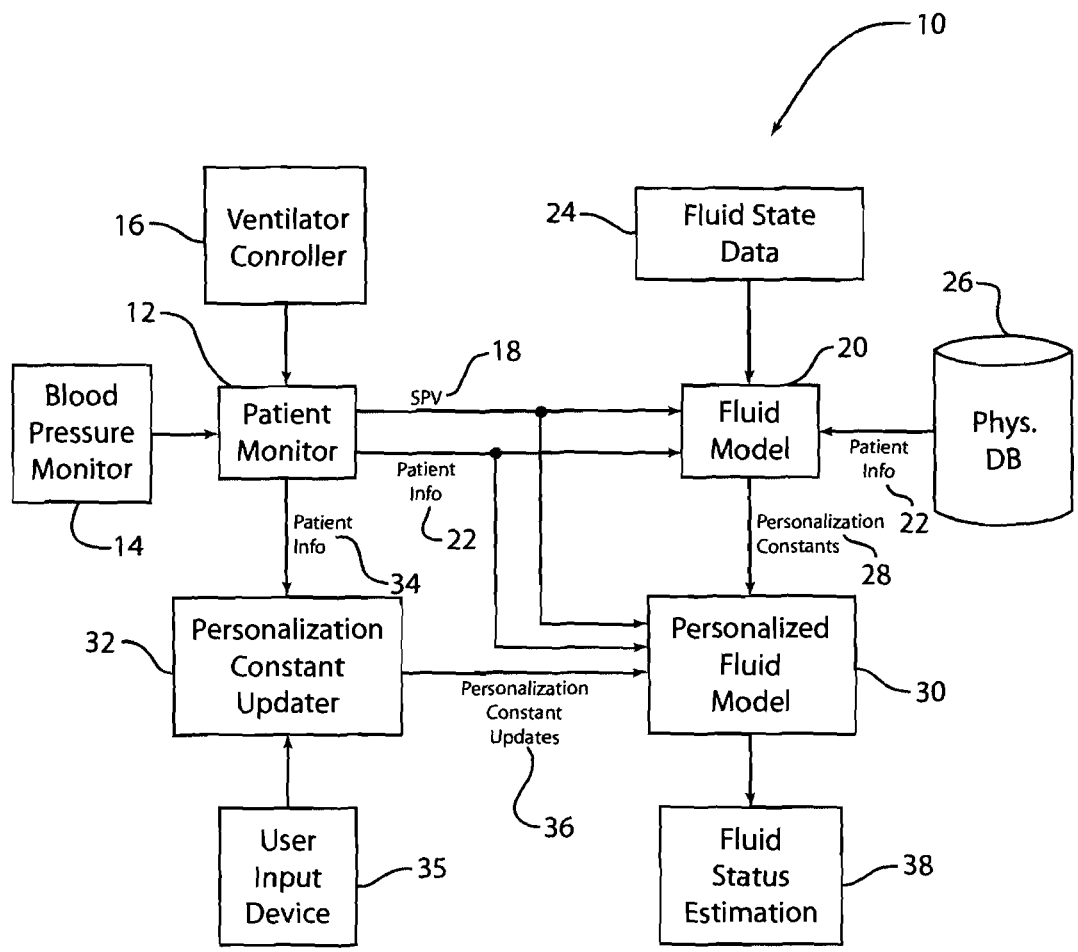
FIG. 1 is a schematic diagram of an embodiment of a fluid assessment system.

FIG. 1 is a schematic diagram depicting an embodiment of a fluid assessment system 10. The fluid assessment system 10 includes a patient monitor 12. The patient monitor 12 comprises one or more patient monitors or other medical devices used to treat one or more physiological conditions of the patient. The patient monitor 12 may include, or be connected to, a blood pressure monitor 14 that monitors the patient blood pressure. In an embodiment, the blood pressure monitor 14 may be an arterial blood pressure monitor, such as a catheter monitor that is inserted into the patient's body and detects the blood pressure of the patient at any of a plurality of locations within the patient's circulatory system. This embodiment produces a physiological signal that is continuous in nature, such that the instantaneous arterial blood pressure may be monitored. Alternatively, an intermittent signal may be produced representative of the patient's instantaneous arterial blood pressure at each cycle of the signal.

The patient monitor 12 further comprises or receives inputs from a ventilator controller 16. The ventilator controller 16 controls the application of mechanical ventilation support to the patient. The controller 16 provides the patient monitor 12 with signals indicative of the ventilation support provided to the patient. Alternatively, the ventilation support provided to the patient may come from another source such as a hand bag and therefore the system 10 should not be limited solely to systems comprising a mechanical ventilator. Alternatively, the signals indicative of the ventilation support provided to the patient may come directly or indirectly from pressure and/or flow sensors (not depicted) disposed within the breathing circuit (not depicted) connected to the patient.

In one embodiment, the patient monitor 12 is connected to at least one additional medical device. The at least one additional medical device may be the blood pressure monitor 14 or the ventilator controller 16, but may be any other medical device for acquiring the physiological data from the patient. The at least one additional medical device may further be a user input device (not depicted) which a clinician may use to enter patient data.

The patient monitor 12 provides a measurement of the patient's SPV as obtained from the signal from the blood pressure monitor 14, to a fluid model 18. Alternatively, the patient's blood pressure may be provided to the fluid model 18 wherein the SPV may be derived. The fluid model 18 may be any type of fluid model as deemed suitable for the presently disclosed application as would be recognized by one skilled in the art. Exemplary embodiments of the fluid model 18 will be discussed in further detail herein. In some embodiments, the fluid model 18 also receives additional patient specific information 22 from the patient monitor 12. The additional patient specific information 22 may include, in some embodiments, machine settings, such as an indication of the application of positive pressure ventilation; or other physiological parameters measured by the patient monitor 12, such as a measured current patient fluid status, respiration rate, or heart rate In a default mode, the fluid model 20 may assume that the patient is in a normovolemic state. The fluid model 20 may also receive fluid state data 24. The fluid state data 24 may indicate a patient fluid state that is not normovolemic. In these instances, the fluid state data 24 (which may be a measurement of current patient fluid volume) would be incorporated into the fluid model 20 to more accurately reflect the patient's current fluid state.

The fluid model 20 may also be connected to a physiological database 26. The physiological database 26 includes historical physiological data of the patient. Such a physiological database 26 may include a patient's electronic medical record (EMR) or may include information relating to additional physiological tests that have been performed on the patient recently. The patient's EMR may include demographic information about the patient and other medical history information. The physiological database 26 provides to the fluid model 20 additional patient specific information 22 such as current patient medications, which may include blood thinning or blood clotting agents; a physiological predisposition to a particular fluid status, such as hemophilia; patient demographic information; or patient medical history information that may help to indicate the patient's current fluid status and/or help to personalize the fluid model.

The fluid model 20 receives some or all of the above-described inputs and uses those inputs to generate personalization constants 28 that are used in the fluid model 20 to tailor the application of the fluid model 20 to the physiological condition of the specific patient. A personalized fluid model 30 is created using the fluid model 20 and the personalization constants 28. The personalization constants 28 may be constant values or algorithms that more accurately describe the physiology of the patient's circulatory system than the more general fluid model 20. The personalization constants 28 may include more detailed definitions of resistances, inductances, and compliances within the patient circulatory system. The personalized fluid model 30 therefore provides a more accurate model representation of the characteristics of the patient's own circulatory system.

In an embodiment, the personalized fluid model 30 may be connected to the patient monitor 12 through a personalization constant updater 32. As time progresses, the physical characteristics of the patient's cardiovascular system may change. Changes to the resistance and/or compliance of the patient's cardiovascular system may come about as a deterioration in the patient's health status, the introduction of new drugs into the patient's system, the loss of fluid by the patient, or many other physiological reasons for a change in cardiovascular properties. The personalization constant updater 32 receives additional patient specific information 34 from the patient monitor 12 and uses this additional patient specific information 34 to provide personalization constant updates 36 to the personalized fluid model 30. The personalization constant updates 36 help to ensure that over time, the personalized fluid model 30 remains an accurate representation of the cardiovascular system of the patient.

Fluid status estimation begins when currently collected SPV data 18 is transferred from the patient monitor 12 to the fluid model 30. Transfer of data can be automatic or initiated by a clinician. The personalized fluid model then applies this newly acquired data to the personalization constants 28, or the personalization constant updates 36 and the equations of the personalized fluid model 30. The applications of the SPV data 18 to the personalized fluid model 30 results in an output of a fluid status estimation 38. The fluid status estimation 38 may be made and presented as either an estimation of patient blood volume or an estimation of relative change in blood volume. The fluid status estimation 38 is visually presented to a clinician. The fluid status estimation 38 may be presented on a graphical display, or may be printed out by a printer. The fluid status estimation 38 may be presented in a textual format to a clinician using e-mail or SMS messaging.

In one embodiment, the fluid status estimation 38 is made using a curve fitting or error limiting technique to "tune" the personalized fluid model 30 to match the contemporaneously monitored SPV 18. A fluid status estimation component of the personalized fluid model 30 is adjusted until the SPV of the personalized fluid model 30 matches that of the contemporaneously monitored SPV 18. The adjusted fluid status that coincides with the matching of the personalized fluid model SPV with the contemporaneously monitored SPV 18 is determined to be the fluid status estimation 38.

Figure 2:
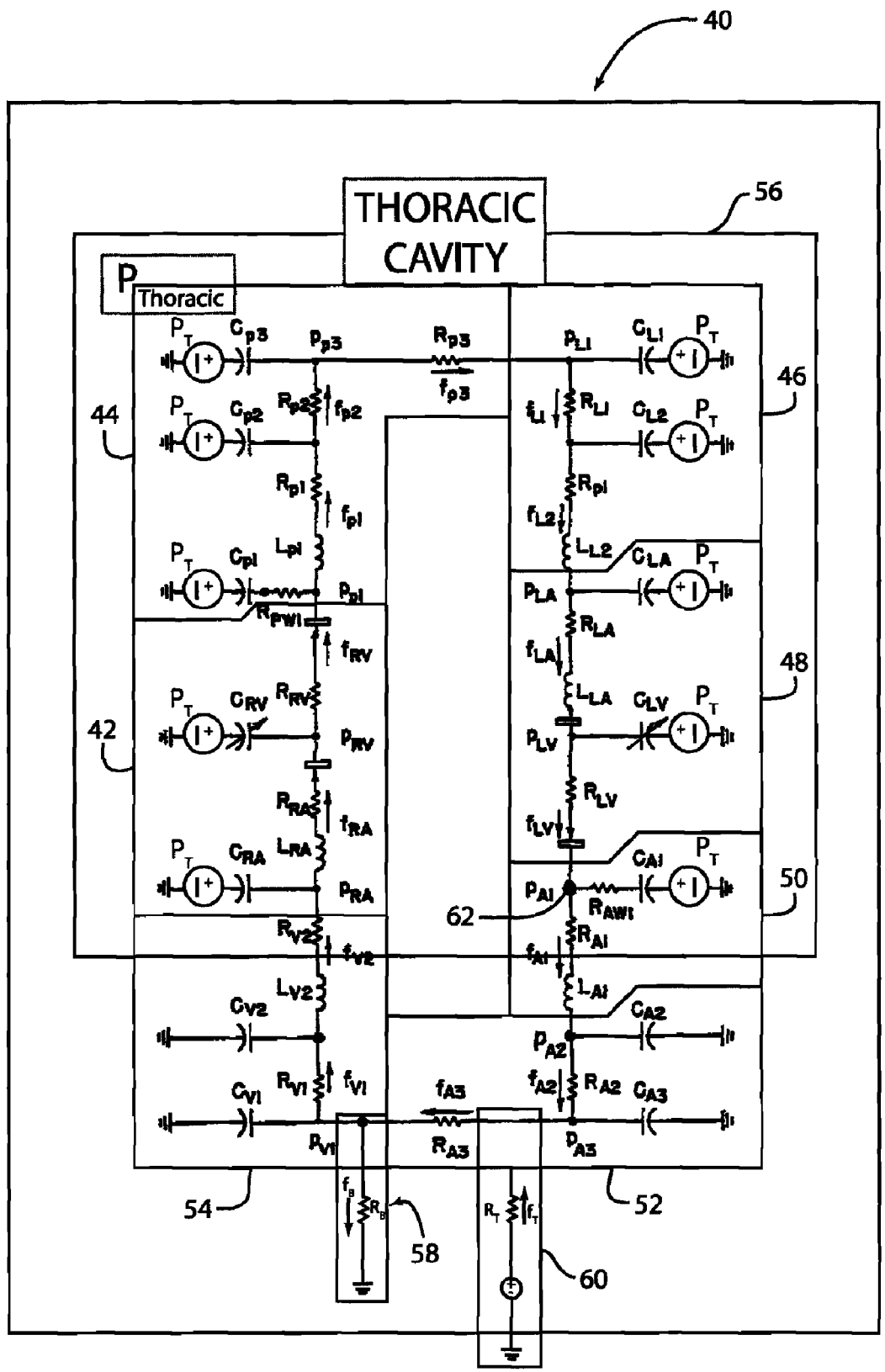
FIG. 2 is a schematic diagram of an embodiment of a fluid model.

FIG. 2 is a schematic diagram of an embodiment of a fluid model 40 used in conjunction with the fluid assessment system 10 as disclosed herein. The fluid model 40 is schematically represented as a circuit comprising a plurality of circuit blocks connected in series and/or parallel to represent the patient's cardiovascular system. The component blocks of the fluid model 40 include the right heart 42, which includes the right atrium and right ventricle, the pulmonary vasculature 44, the lungs 46, the left heart 48, which includes the left atrium and the left ventricle, the aorta 50 the arterial vasculature 52, and the venus vasculature 54. Each of the component blocks comprises one or more capacitors, inductors, or resistors that model the physiological properties of each of the component blocks within the patient's cardiovascular system. Each component block also includes one or more flow and/or pressure notations, each of these being indicative of the blood flow (f) and blood pressure (P) in the associated physiological component within the patient.

As mentioned earlier, during PPV an additional pressure is applied to the thoracic cavity of the patient. This results in changes to the hemodynamic properties within the patient's cardiovascular system. In the fluid model 40, the addition of PPV to the patient is represented by the addition of voltage sources ($P_T$) to each of the patient physiological components that are located within the thoracic cavity 56. Voltage waveforms representative of the cyclically changing intra-thoracic pressure can be applied to each of the voltage sources $P_T$. These voltage waveforms can be modified to accurately reflect the intra-thoracic pressure generated based on the mechanical ventilation delivered to the patient and/or patient physiological characteristics such as chest wall compliance.

As depicted in FIG. 2, the fluid model 40 is one example of the fluid model 20 used in the previously described fluid assessment system 10. As stated above, by solving for one or more of the variables in fluid model 40 and replacing them with personalization constants, the fluid model 40 can be personalized to more accurately reflect the physiological properties of that specific patient. Thus, the fluid model 40 can be modified to create the personalized fluid model 30.

As described above with respect to FIG. 1, the personalization constant updater 32 provides updated personalization constants 36 to the personalized fluid model 30. While this may incorporate updates of physiological data such as would result in the modification of one or more of the personalization constants, another type of update may be a physiological change that must be added to the personalized fluid model. Such physiological change may include that of a patient bleeding which may be represented by the simulated bleeding component 58. The simulated bleeding component 58 is modeled with the proper resistance ($R_b$) and flow ($F_b$) values such as to model a patient that is actively losing blood at a known rate ($F_b$). Such an addition to the fluid model 40 further helps to more accurately represent the current fluid status of the patient.

Similarly, a simulated infusion component 60 can be added to the fluid model 40 such as to represent the known infusion of fluid into the patient's cardiovascular system at a known flow rate. Thus, simulated infusion component may include a resistance ($R_t$) at a known flow ($f_t$) as with the simulated bleeding component 58, the addition of a simulated infusion component 60 may help to provide a more accurate reflection, and resulting estimation, of the patient's current fluid status.

In order to correlate the fluid model 40 to the measured SPV from the patient, the proper location and physiological component for the SPV measurement must be located within the fluid model 40. Often, arterial blood pressure is taken via a catheter from the patient's aorta. As such, for exemplary purposes, this pressure location coincides with reference point 62 located within the aorta component 50 of the fluid model 40.

Thus, the pressure at reference point 62 may be used in two ways in conjunction with the fluid model 40. First, the fluid model 40 may be used in a predictive fashion in order to estimate the continuous blood pressure and thus the SPV measured at the aorta for a patient who experiences a specific amount of blood loss. Alternatively, the patient's measured continuous blood pressure may replace the variable value of the pressure at reference point 62, and the model can be used to estimate blood loss or personalized constants.

If the patient's fluid loss is unknown, then the fluid model 40 is tuned in order to determine a value for the reduced volume of blood in the cardiovascular system or may be tuned to identify the flow rate of blood loss in the simulated bleeding component 58.

While the fluid model 40 has been used in an exemplary fashion, the fluid models as used in the herein disclosed system and method are not so limited to the specific fluid model 40 disclosed. The fluid model used may be significantly more or less complex than the exemplary fluid model 40. Any of the fluid models as would be recognized by one skilled in the art could be suitable in embodiments depending upon the specificity desired by the model and the available known inputs that may be added to the model in order to personalize the model for the patient.

Figure 3:
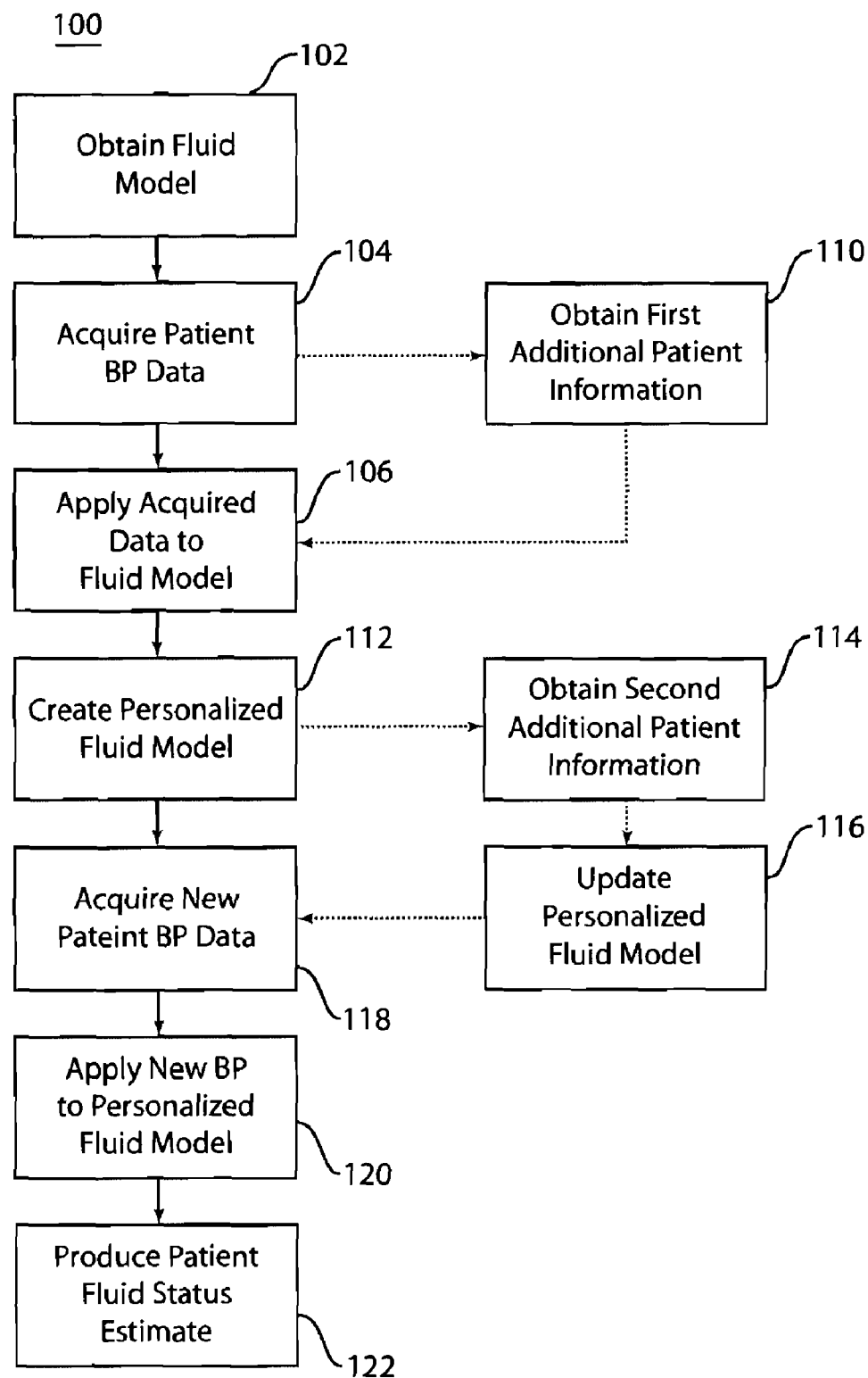
FIG. 3 is a flow chart depicting the steps in an embodiment of a method of providing personalized fluid assessment.

FIG. 3 is a flow chart depicting the steps of an embodiment of a method of providing a personalized fluid assessment 100.

First, at step 102 a fluid model is obtained. The fluid model may be locally stored on a device that may be used in conjunction with the disclosed method. Alternatively, the fluid model may be stored at a remote location such that the fluid model must be obtained in step 102 via a communications platform such as the Internet, telecommunications, or an IT network. In a still further embodiment, the fluid model can be physically entered or defined by the clinician at the start of performing the method 100.

Next, patient blood pressure data is acquired in step 104. Typically, this blood pressure data is continuous blood pressure data, as may be obtained through an arterial catheter. Alternatively, the blood pressure data is acquired intermittently, but at regular intervals at a relatively frequent rate (i.e., 0.1 Hz or greater). In an exemplary embodiment, the acquired blood pressure data is continuous blood pressure data spanning at least one breath cycle. The blood pressure data acquired in step 104 may further include a determination of the patient SPV as obtained from the acquired blood pressure data.

The blood pressure data acquired in step 104 is then applied to the fluid model in step 106. In alternative embodiments, first additional patient information parameter is obtained beyond the patient blood pressure data acquired in step 104. This additional patient information is acquired in step 110. The obtained first physiological data in step 110 may include an identification of whether or not the patient is receiving positive pressure ventilation, an indication of the airway pressure that is delivered to the patient, the patient's demographic information, medical history, other monitored physiological parameters, or machine settings. Alternative types of first additional patient information that may be acquired at step 110 may include a measure of the patient's chest wall compliance, information regarding current drugs the patient is receiving, or other information regarding patient preexisting conditions. The first additional patient information may be obtained by the same patient monitor device that acquires the patient blood pressure data, or may be obtained from another device or entered manually by a clinician.

In step 106, all of the data acquired in step 104 and optionally in step 110 are applied to the fluid model obtained in step 102. By applying the acquired data to the fluid model, particular values in the fluid model are defined such as to represent the current fluid status and physiological condition of the patient. These defined values are referred to as personalization constants. The end result of the application of the acquired data to the fluid model in step 106 is to create a personalized fluid model in step 112. The personalized fluid model created in step 112 includes the personalization constants that have been derived to more accurately reflect the status and physiological condition of the patient based upon the data acquired in step 104 and/or step 110.

Next, in optional steps, second additional patient information may be obtained in step 114. This second additional patient information may be acquired at a later time or date, especially at a time or data proximal to when the personalized fluid assessment is desired. The second additional patient information obtained in step 114 is then used in step 116 to update the personalized fluid model created in step 112. This provides an advantage in that the personalized fluid model created in step 112 is updated in step 116 to account for changes in the patient fluid status or physiological condition that have occurred since the personalized fluid model was created in step 112. The inclusion of these changes in fluid status or physiological condition may help to improve the accuracy of the personalized fluid assessment produced in embodiments of the method disclosed herein.

Next, regardless of whether the personalized fluid model created in step 112 or the updated personalized fluid model from step 116 is used, in step 118 new patient blood pressure data is acquired. The new patient blood pressure data most accurately reflects the physiological status of the patient at the time when the personalized fluid assessment is desired. The newly acquired blood pressure data may also include a determination of the blood pressure SPV as well.

Next, in step 120, the newly acquired blood pressure data is applied to the personalized fluid model from either step 112, or optionally step 116. By the introduction of the newly acquired blood pressure data into the personalized fluid model, the fluid model may be used to derive an estimate of the patient's current blood volume, and or blood volume change, based upon the measured blood pressure and the SPV. Thus, in step 122, a patient fluid status estimate is produced.

The new blood pressure data is applied to the personalized fluid model in step 120 by comparing a derived value of the blood pressure SPV from the personalized fluid model to the SPV of the newly acquired blood pressure data. The personalized fluid model is then modified to adjust the patient fluid volume status in order to match the derived SPV with the currently measured SPV using a curve fitting or error limiting technique. One such curve fitting or error limiting technique that may be used in the comparison of the derived and the measured SPV values is that of a minimum square error technique. The fluid status of the personalized fluid model is adjusted until the derived SPV and the newly acquired SPV match. The fluid status used in the personalized fluid model when a match is achieved is the estimated fluid status for the patient produced in step 122.

Some embodiments of the system and method as disclosed herein may be implemented solely through the use of a computer. Such embodiments may be implemented through the use of computer readable code stored on a computer readable medium. Such computer readable code may define modules, or sub-programs that perform the step of an embodiment of the method as disclosed herein. In such computer implemented embodiments, the technical effect of the system and method as disclosed herein may be that of providing a personalized fluid assessment based upon one or more readily obtainable patient physiological parameters.

Embodiments of the system and method as presented disclosed may further provide the advantage of providing a single fluid status indicator that may be used to normalize patient fluid status monitoring techniques. Such embodiments may provide the advantage of providing an indication of fluid status in a less invasive manner then some previously implemented techniques. Embodiments as disclosed herein may also present the advantage of providing fast and accurate assessment of a patient's fluid status that is not labor intensive on the part of the clinician.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent elements with insubstantial differences form the literal languages of the claims.

Various alternatives and embodiments are contemplated as being with in the scope of the following claims, particularly pointing out and distinctly claiming the subject matter of the present disclosure.

What is claimed is:

1. A method of estimating the fluid status of a patient, the method comprising the steps of:
   obtaining a fluid model;
   acquiring first blood pressure data from the patient;
   creating a personalized fluid model for the patient by calibrating the fluid model to reflect the first blood pressure data;
   acquiring a second blood pressure data;
   applying the acquired second blood pressure data to the personalized fluid model; and
   producing an estimated patient fluid status.

2. The method of claim 1 further comprising obtaining first additional patient information wherein the personalized fluid model reflects the first blood pressure value and the first additional patient information.

3. The method of claim 2 wherein the first blood pressure data is first dynamic blood pressure data and the second blood pressure data is second dynamic blood pressure data.

4. The method of claim 2, wherein the first additional patient information is an indication of the application of positive pressure ventilation to the patient.

5. The method of claim 3, wherein the fluid model comprises at least one personalization constant and the step of creating the personalized fluid model includes deriving the value of at least one personalization constant.

6. The method of claim 5, wherein the value of the personalization constant is derived using the first additional patient information and the first blood pressure data.

7. The method of claim 6, wherein the personalization constant is a mathematical value of a parameter from the fluid model.

8. The method of claim 7, wherein the personalization constant is a physiological compliance.

9. The method of claim 5, further comprising the steps of:
   obtaining second additional patient information;
   deriving at least one updated personalization constant from the second additional patient information; and
   applying the at least one updated personalization constant to the personalized fluid model.

10. The method of claim 9, wherein the second additional patient information is indicative of the application of positive pressure ventilation to the patient.

11. The method of claim 3 wherein the first blood pressure data comprises first systolic pressure variation data and the second blood pressure data comprises second systolic pressure variation.

\* \* \* \* \*